US007090806B1

(12) United States Patent
Lenehan

(10) Patent No.: US 7,090,806 B1
(45) Date of Patent: Aug. 15, 2006

(54) PORTABLE OXYGEN SENSOR ANALYZER

(76) Inventor: Peter Lenehan, 22721 La Quinta Dr., Mission Viejo, CA (US) 92691

( * ) Notice: Subject to any disclaimer, the term of this patent is extended or adjusted under 35 U.S.C. 154(b) by 771 days.

(21) Appl. No.: 09/845,513

(22) Filed: Apr. 30, 2001

Related U.S. Application Data

(60) Provisional application No. 60/200,917, filed on May 1, 2000, provisional application No. 60/227,253, filed on Aug. 23, 2000, provisional application No. 60/243,971, filed on Oct. 27, 2000.

(51) Int. Cl.
*G01N 27/00* (2006.01)
*G01N 31/10* (2006.01)
*G01N 33/22* (2006.01)

(52) U.S. Cl. .................... 422/83; 422/94; 422/98; 422/105; 436/127; 436/37; 436/143

(58) Field of Classification Search .............. 422/83, 422/94, 98, 105, 168; 436/37, 122, 143

See application file for complete search history.

(56) References Cited

U.S. PATENT DOCUMENTS

| 3,745,768 A | 7/1973 | Zechnall et al. |
| 3,938,075 A | 2/1976 | Reddy |
| 3,948,228 A | 4/1976 | Luchaco |
| 4,149,408 A | 4/1979 | Ezoe et al. |
| 4,622,844 A * | 11/1986 | Bienkowski ................ 73/1.06 |
| 4,831,560 A | 5/1989 | Zaleski |
| 4,878,380 A | 11/1989 | Goodman |
| 5,001,432 A | 3/1991 | Wixon |
| 5,027,646 A | 7/1991 | Mizutani et al. |
| 5,083,427 A * | 1/1992 | Anderson .................... 60/274 |
| 6,135,101 A | 10/2000 | Konno et al. |

* cited by examiner

*Primary Examiner*—Lyle A. Alexander
(74) *Attorney, Agent, or Firm*—Denton L. Anderson; Sheldon & Mak PC

(57) ABSTRACT

A portable, inexpensive, and easy to operate vehicle oxygen sensor analyzer shows, in real time, on an ultra-bright LED display, the dynamic operation of the oxygen sensor, simulates sensor signals into the computer, while monitoring the oxygen sensor to confirm correct computer operation, and performs a quick, simple and accurate test on the oxygen sensor to prove that it will pass emissions tests for oxygen sensors of the type typically required under emissions control regulations.

10 Claims, 3 Drawing Sheets

PORTABLE OXYGEN SENSOR ANALYZER

BACKGROUND OF THE INVENTION

This invention relates generally to diagnostic equipment for vehicle engines, and more particularly to portable and convenient oxygen sensing equipment for verifying that the on-board oxygen sensor is operating correctly, and in accordance with emissions control regulations.

Most computer controlled gasoline vehicle engines are equipped such that the air-fuel ratio is controlled by a 0–1 V oxygen sensor as specified, for example, in U.S. Pat. No. 3,745,768. Such oxygen sensors are required to operate from a maximum of 175 mV (lean) to a minimum 800 mV (rich) and should be able to move between these voltage limits, from lean to rich, within 100 mS as detailed in emissions regulations, such as those set forth in the California Bureau of Automotive Repairs Oxygen Sensor Test. The ideal stoichiometric condition of 14.7 to 1 is approximately 500 mV, which the on-board control computer tries to maintain by cutting back on fuel when the oxygen sensor reads rich and increasing fuel when the oxygen sensor reads lean. The oxygen sensor is the primary feedback sensor controlling emissions and fuel mileage and it is important that it is operating correctly. Late model cars with OBD2 (On-Board Diagnostics 2) emissions control equipment (required by the Federal Government since 1996) may be able to identify slow or faulty sensors, but pre-1996 automobile on-board diagnostic systems (OBD1 systems) only have the capability to detect catastrophic failures.

To test this on-board oxygen sensor, to ensure operation within emissions control regulations, the California Bureau of Automotive Repairs Oxygen Sensor-Test, for example, requires that propane be fed into the air intake to enrich the engine, so that when the flow of propane is turned off, the engine will go lean and the oxygen sensor signal will fall below 175 mV. When this is observed on an expensive digital storage oscilloscope (DSO), the throttle is snapped, forcing the engine to go rich very quickly. The oxygen sensor signal must exceed 800 mV within 100 mS of moving above 175 mV, as measured on the oscilloscope using 100 mS/Div time base, or it is considered slow or faulty, and should be replaced. With some 4-wire oxygen sensing systems, which can cost in excess of $300, an accurate test is essential, but this official test, although it is required for smog technicians, is time consuming because of the propane usage requirement, and accurate to only about 20%, when trying to read 100 mS on a single division. As a result, most oxygen sensors are replaced on a whim, a guess, or according to arbitrary vehicle mileage levels. This is a very expensive and unnecessary approach for the consumer, particularly if this arbitrary course of action does not resolve the actual emissions system problem. Many technicians try to diagnose the condition of an oxygen sensor with a scanner, such as that disclosed in U.S. Pat. No. 4,831,560, but since these use the ALDL serial data diagnostic link, which comprises an under-dash serial data port required as standard equipment in automobiles under U.S. regulations, with perhaps 500 mS update times, they can only capture a voltage on a random basis, and cannot identify a bad oxygen sensor, unless its failure is catastrophic. Also, they cannot show real time operation of the oxygen sensor, where other engine faults can be seen, especially while the vehicle is being operated, and do not have any capability of simulating to the computer to confirm correct operation.

SUMMARY OF THE INVENTION

The present invention comprises an oxygen sensor analyzer that shows, in real time, on an ultra-bright Light Emitting Diode (LED) display, the dynamic operation of the oxygen sensor, simulates sensor signals into the computer, while monitoring the oxygen sensor to confirm correct computer operation, and do a quick, simple and accurate test on the oxygen sensor to prove that it will pass the official California Bureau of Automotive Repairs Oxygen Sensor Test. It is equally effective in confirming the passage of other regulatory tests as well. It has been found to be accurate to within about 5%, and meets the California Bureau of Automotive Repairs 100 mS Test, for example, without the use of time-consuming propane, giving a PASS or FAIL result which removes the decision from the hands of the technician.

A low cost, hand-held oxygen sensor analyzer is provided which has three modes of operation. The first is a closed loop oxygen sensor monitor, which shows, in real time, on an ultra-bright display comprised of a plurality (preferably ten) of LED's disposed in series, the dynamic operation of the oxygen sensor. This can be safely seen at a glance, while driving, allowing easy diagnoses of dirty mass air flow sensors, bad fuel pumps, and plugged fuel filters. The second mode simulates oxygen sensor signals to the computer, while monitoring the real oxygen sensor to see the reaction to the simulation, allowing reaction times and correct operation of the computer to be confirmed. The third mode performs the official oxygen sensor test, without the requirement of using propane to force the engine lean, thus saving much time.

In the third mode, a 950 mV signal is sent to the computer, forcing the engine lean, and sending the oxygen sensor signal below 175 mV. A start button is pressed, permitting the test to begin by snapping the throttle, forcing the engine rich quickly. A 100 mS timer starts as the signal exceeds the lowest LED (<175 mV) in the series, also changing the simulated signal to 50 mV, and if the signal reaches the top LED (>800 mV) before the timer times out, a "Pass" is indicated. If it does not reach the top LED in the series, or is slow (meaning that it does not reach that LED before the timer times out, then a "Fail" is indicated. If the sensor repeatedly fails and slow engine response is a concern, then a blast of propane in the air intake, instead of snapping the throttle, may permit the sensor to pass by eliminating engine variables. This fast, automatic test makes it easy for even an inexperienced technician to accurately (within 5%) identify a faulty oxygen sensor, using the "Pass" or "Fail" indicators, thus saving vehicle repair shops and customers significant expense.

More particularly, there is provided an oxygen sensor analyzer for use in testing the performance of an oxygen sensor comprising a portion of a vehicle emission system having an on-board computer. The inventive oxygen sensor analyzer comprises a housing having a keypad, which has a plurality of keys and indicator lights disposed thereon. The oxygen sensor analyzer is capable of a plurality of modes of operation. It comprises a closed loop oxygen sensor monitor mode, for showing, in real time, the dynamic operation of the oxygen sensor being tested, as well as a simulated oxygen sensor mode, for simulating oxygen sensor signals to the vehicle computer, while monitoring the oxygen sensor for its reaction to the simulation. A third mode is an oxygen sensor test mode, for performing an oxygen sensor test which forces the engine to run lean without the need for injecting propane thereinto.

In another aspect of the invention, there is provided a portable oxygen sensor analyzer for use in testing the performance of an oxygen sensor comprising a portion of a vehicle emission system having an on-board computer. The oxygen sensor analyzer comprises a housing having a keypad, which has a plurality of keys and indicator lights disposed thereon. Additionally, means are provided for evaluating the oxygen sensor's performance relative to pre-established acceptable standards. The inventive portable oxygen sensor analyzer is connectable in series with the oxygen sensor and the on-board computer, such that the analyzer may be operated while connected within a passenger compartment of the vehicle.

In yet another aspect of the invention, there is disclosed a method for testing the performance of an oxygen sensor comprising a portion of a vehicle emission system having an on-board computer. The inventive method comprises a step of connecting an oxygen sensor analyzer, which comprises a keypad having a plurality of keys and indicator lights disposed thereon, and circuitry permitting the testing of the oxygen sensor in a plurality of different operating modes, in series with the oxygen sensor and the on-board computer. Once connected, the oxygen sensor analyzer is activated to operate in one of the operating modes to test the oxygen sensor. A particularly advantageous step is to evaluate the performance of the oxygen sensor without the use of a Digital Storage Oscilloscope.

The invention, together with additional features and advantages thereof, may best be understood by reference to the following description taken in conjunction with the accompanying illustrative drawing.

DESCRIPTION OF THE PREFERRED EMBODIMENT

Figure 1:
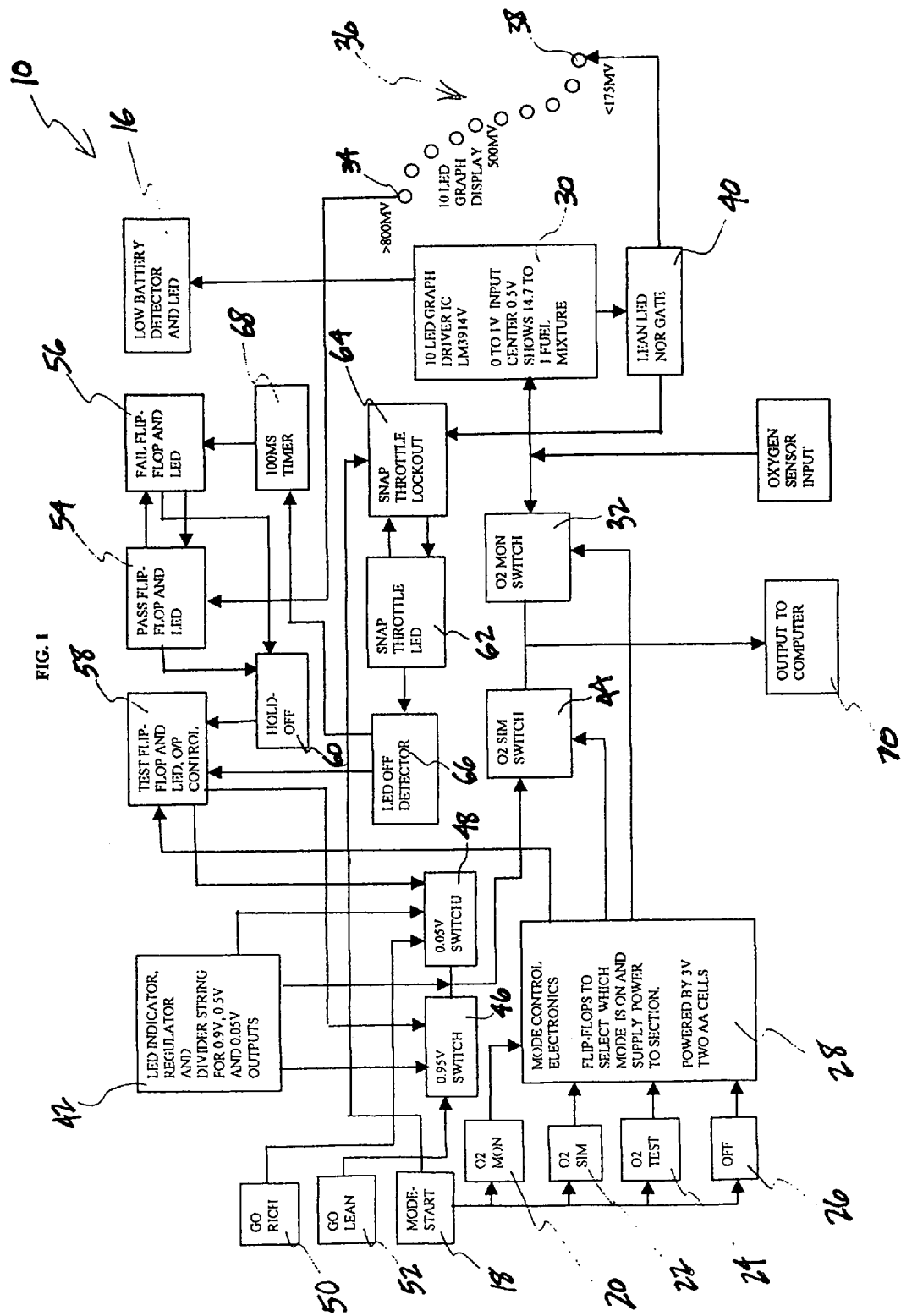
FIG. 1 is a block diagram showing the operation of an oxygen sensor analyzer constructed in accordance with the principles of the present invention.
Figure 2:
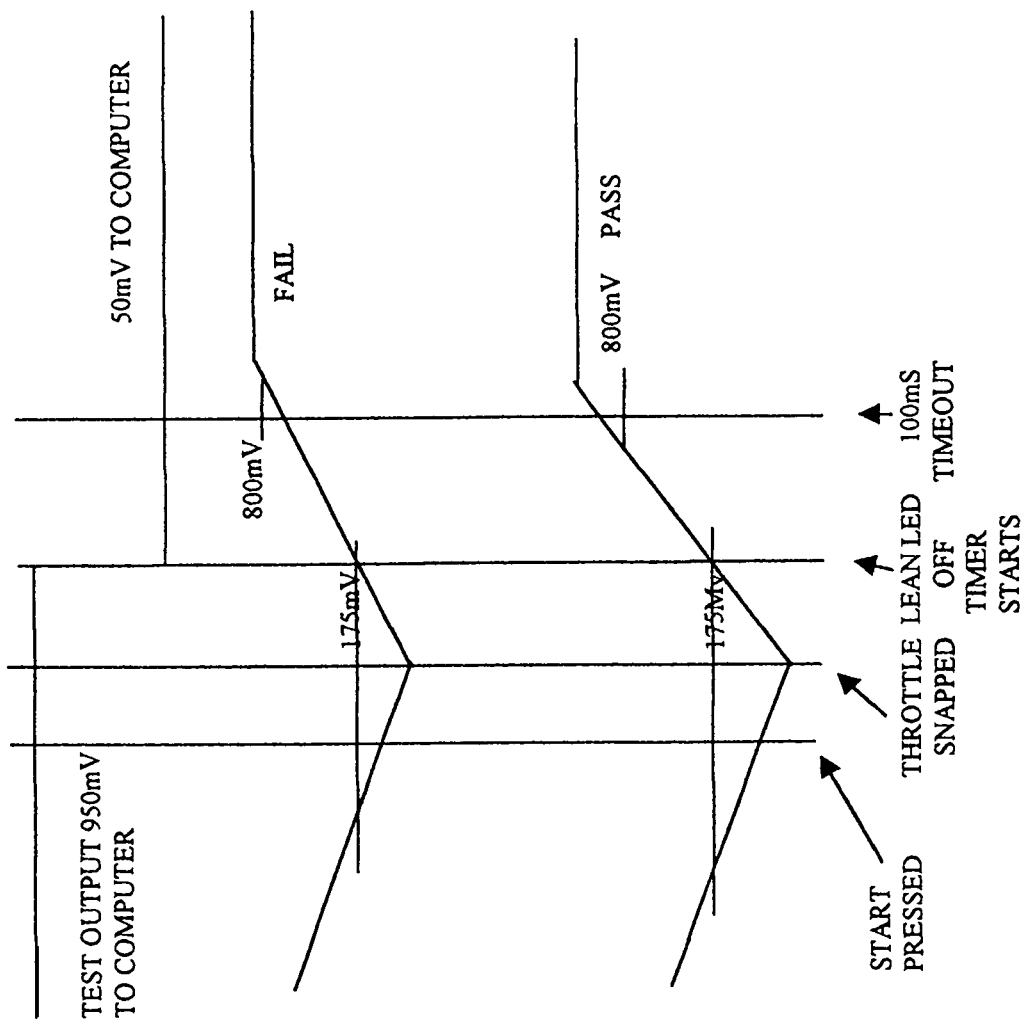
FIG. 2 is a timing diagram showing how the oxygen sensor test performed in accordance with the inventive method analyzes an oxygen sensor using "Pass" or "Fail" standards.
Figure 3:
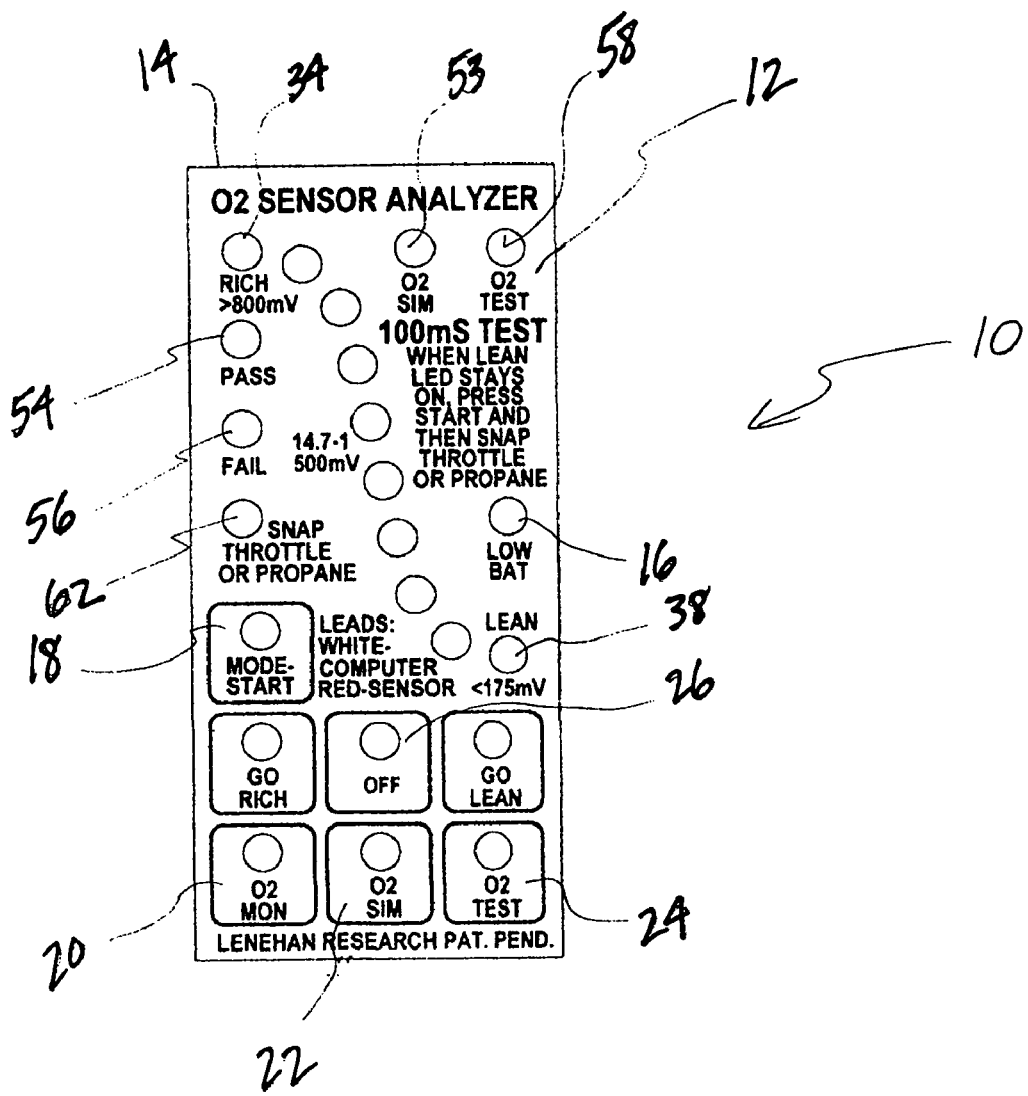
FIG. 3 is a diagram of a membrane keypad for the oxygen sensor analyzer of the present invention, with ports for the LED display and status LED's.

Referring now more particularly to FIGS. 1–3, there is illustrated a hand-held oxygen sensor analyzer 10 having a keypad 12 disposed on a front surface of a housing or case 14. The hand-held instrument 10 is preferably powered by 3 volts, using two AA batteries (not shown) disposed in a compartment in the back of the case 14. A low battery detector LED 16 is activated when the battery voltage falls below 2.5 V. The housing 14 is preferably manufactured of black ABS, although other suitable materials, whether plastic, metal, or otherwise, may be employed as well. The keypad 12 is preferably a membrane keypad, with clear ports for each of the LED indicators on the front.

To eliminate accidental activation, such as when the instrument 10 is in a toolbox, or while in use, the "MODE-START" key must be depressed simultaneously with any of the four mode keys, which include the $O_2$ MON (Monitor) key 20, the $O_2$ SIM (Simulate) key 22, the $O_2$ TEST key 24, and the OFF key 26. Since the operation is activated by momentary keypads, all mode control is accomplished by flip-flop circuits 28, which power the required sections and turn on appropriate switches. In the $O_2$ MON mode, an LED graph driver 30, the low battery detector LED 16, and an $O_2$ MON switch 32 are activated, permitting the oxygen sensor, while connected to the computer, to be observed. The top rich LED 34 of a ten LED sequential array 36 is set to activate at just above 800 mV, while the bottom lean LED 38 is activated at just below 175 mV. The center LED's in the array 36 switch over at 500 mV. The LED graph driver 30 preferably comprises an LM3914 integrated circuit chip, available from National Semiconductor (though other chips of similar capability can be substituted), which normally turns off the lowest LED at below 80 mV, a level that is not practical as a reference for the test. A nine input NOR gate 40, connected to the other LED's in the array 36, turns on the LED 38, if all of the other LED's are off, allowing it to indicate when the signal is below 175 mV. This LM3914 graph chip is made up of ten comparators driving each of the ten LED's, and is an excellent reference now, for the $O_2$ test, for both high and low levels, and at any level at least one LED will be lit to indicate that $O_2$ MON is running.

The $O_2$ SIM mode permits the oxygen sensor to be monitored while disconnected from the computer by the switch 32, and voltages from a divider string and LED indicator regulator 42, that simulate the oxygen sensor, are sent to the computer by an $O_2$ SIM switch 44, and are controlled by switches 46 and 48, activated, in turn, by GO LEAN and GO RICH keypads 52 and 50, respectively, feeding 950 mV, 50 mV, or 500 mV (both off). Accordingly, the divider string 42 is configured for 0.9 V, 0.5 V, and 0.05 V outputs. This mode can be used for tune up, identifying computer-engine reaction times, and confirming correct computer operation. An $O_2$ SIM LED 53, when lit, signifies the operation of the instrument 10 in the $O_2$ SIM mode.

The $O_2$ TEST mode is designed to give an accurate 100 mS test, checking speed and voltage limits, and showing the result with a PASS LED 54 or a FAIL LED 56. When the $O_2$ TEST key 24 is depressed, TEST flip-flop and LED 58 are activated, which holds off through "Hold-Off" circuit 60 the PASS and FAIL flip-flops 54 and 56, respectively, while at the same time feeding 950 mV to the computer through switches 46 and 44. This rich voltage eliminates the need for using propane to do the same thing through the oxygen sensor. This voltage forces the computer and engine to go lean, causing the oxygen sensor reading to drop below 175 mV, thereby turning on the lowest led LED 38 through the 9-input NOR gate 40. In order to eliminate erroneous tests caused by oscillating signals, a "SNAP THROTTLE" LED 62 and later test circuitry is locked off by Snap Throttle Lockout 64 until the MODE-START key 18 is depressed, when the lowest lean LED 38 is staying on, permitting the Snap Throttle LED 62 to light, readying it for the test. The technician snaps the throttle, causing the computer and engine to go instantly rich and the oxygen sensor output rises. When the lean LED 38 and the Snap Throttle LED 62 go out, LED off detector 66 sends a signal to the TEST LED 58 and to a 100 mS timer 68 to start it. The TEST LED 58 is now turned off, which changes the voltage to the computer to 50 mV through switches 48 and 44, and allows PASS and FAIL flip flops 54 and 56, respectively, to wait for a signal from either the top rich LED 34 (>800 mV) or time out from the 100 mS timer 68. If the oxygen sensor is slower to reach the >800 mV LED, or does not reach it, the 100 mS timer 68 will time out and turn on the FAIL LED 56, locking out the PASS LED 54.

The inventor has found that the foregoing control and logic can also be achieved using an embedded microprocessor and firmware or ASICS (Application Specific Integrated Circuits) or PLDS (Programmable Logic Devices). FIG. 2 illustrates a timing diagram for the output to the computer 70, the fail timing, and the pass timing. This tester can be manufactured within 5% accuracy, but can be calibrated to better than 1% accuracy. This novel test shows that it can achieve the same results of the official California Bureau of Automotive Repairs test, while doing it quicker and safer (no propane hook up), and with much higher accuracy and ease of use than a DSO. All the LED's used are high brightness to be visible in sunlight and can be seen at a glance more safely, when driving, than a DSO.

Operation of the described oxygen sensor analyzer system will now be described in greater detail. As noted supra, at present most oxygen sensors are replaced according to the number of miles on them, or merely on a whim or informed guess, if the emissions system is experiencing problems meeting regulatory standards. With the prices for 4-wired oxygen sensors approaching, in some instances, $300, this is an expensive proposition, particularly if replacement does not solve the diagnosed problem.

The instrument 10 is equipped with a pair of leads (not shown), preferably of TEFLON® material, which are six feet long. This permits the leads to withstand temperatures of up to 400 degrees F., and the instrument to be operated from inside of the passenger compartment, for use while driving. When it is desired to perform any of the available tests, described above, the $O_2$ sensor connector near the sensor (which connects the sensor to the on-board computer) is disconnected. Then, the red lead is connected to the $O_2$ sensor output pin, using available red adapters if necessary (many sensors use black wire as output and white wires for the heater). The white lead is then connected to the $O_2$ signal input pin to the computer using white adapters, if necessary.

At this juncture, the black clip (not shown) is connected to a clean engine ground away from heat, or to a black adapter for 4-wire sensors. Now the instrument 10 has been fully installed, in series between the $O_2$ sensor and the on-board vehicle computer. Once fully connected to the system, the MODE-START key 18 is depressed simultaneously with the $O_2$ MON key 20 to monitor the $O_2$ sensor in closed-loop mode, as described above. This mode permits the display of the dynamic operation of the oxygen sensor in real time (as compared to a scanner), while in closed loop connection with the computer. If the computer is in closed loop, the signal will be seen to vary continuously above and below the center, oscillating between 1 and 20 Hz, typically. Because of the six foot leads, and the consequent ability to operate the instrument within the passenger compartment, while driving, many problems can be seen safely on the ultra-bright LED display, showing leanness on acceleration, for example, indicating a dirty mass air flow sensor, a bad fuel pump, or perhaps a clogged fuel filter.

Alternatively, by depressing the MODE-START key 18 simultaneously with the $O_2$ SIM key 22, the $O_2$ SIM mode is activated. This mode still shows the sensor signal, while sending a separate simulated sensor signal to the computer, allowing correct computer operation to be checked. By holding down the GO RICH keypad 50 or the GO LEAN keypad 52, computer reaction will be seen on the oxygen sensor display. When no keys are depressed, 0.5 V is sent to the computer, allowing easy mass air flow tune-up on older cars.

For the $O_2$ TEST MODE, the MODE-START key 18 is depressed simultaneously with the $O_2$ TEST key 24. This mode will do a fast, accurate (within 5%) 100 mS test on the oxygen sensor, indicating PASS or FAIL. With the $O_2$ TEST light 58 lit, a "go lean" signal of 950 mV is sent to the computer, forcing the engine lean. When the LEAN LED 38 is continuously lit, the MODE-START key 18 is depressed once again, at which juncture the SNAP THROTTLE OR PROPANE LED 62 is illuminated, indicating that the instrument is ready to do the test. At this point, the throttle is quickly snapped, such that the resultant fast enrichment should cause the oxygen sensor signal to jump from the LEAN LED 38 (<175 mV) to the RICH LED 34 (>800 mV). If this transition occurs in less than 100 mS, the PASS LED 54 will light. If it is too slow, or does not reach >800 mV, the FAIL LED 56 will light. The test can be repeated as desired by again depressing the MODE-START and $O_2$ TEST keys simultaneously. If the test fails repeatedly, then a blast of propane can be introduced into the air cleaner, when the SNAP THROTTLE OR PROPANE LED is lit, to quickly enrich the engine directly, without the variables of slow engine response, or the like, possibly allowing the $O_2$ sensor to pass the test.

It should be noted that, although the preferred instrument 10 is particularly adapted to the California Bureau of Automotive Repairs 100 mS test, it may be re-programmed or adapted to satisfy the requirements any other such test, well within the range of one of ordinary skill in the art.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. It is intended that the scope of the invention be limited not by this detailed description, but rather only by the claims appended hereto.

What is claimed is:

1. An oxygen sensor analyzer for use in testing the performance of an oxygen sensor comprising a portion of a vehicle emission system having an on-board computer, the oxygen sensor analyzer comprising:
    (a) an electronic circuit having an oxygen sensor input for receiving an oxygen sensor signal from the oxygen sensor with the oxygen sensor disconnected from the on-board computer, a simulate output for connection to the on-board computer in place of the oxygen sensor, and logic means operative for driving the simulate output in:
        (i) a closed-loop mode wherein the simulate output directly follows the oxygen sensor input; and
        (ii) a simulate mode wherein the simulate output, being isolated from the oxygen sensor input, is driven in an arbitrary manner for forcing the engine to run one or both of lean by driving the simulate output to simulate a rich indication from the oxygen sensor, and rich by driving the simulate output to simulate a lean indication from the oxygen sensor; and
    a display for indicating the oxygen sensor signal.

2. The oxygen sensor analyzer of claim 1, wherein the logic means is further operative for:
    (a) driving the simulate output in a test mode wherein the simulate output, being isolated from the oxygen sensor input, is driven in a predetermined manner that includes forcing the engine to run lean by driving the simulate output to simulate a rich indication from the oxygen sensor; and
    (b) monitoring the oxygen sensor input to measure time-response thereof between conditions of the engine running lean and running rich.

3. The oxygen sensor analyzer of claim 2, wherein the logic means is further operative for signaling a ready condition in the test mode wherein the oxygen sensor input is indicative of the engine having reached a stable lean operating condition, and subsequently enabling the measure of time response when the oxygen sensor input is indicative of engine operation passing from lean toward rich.

4. The oxygen sensor analyzer of claim 3, wherein the oxygen sensor input is responsive over a voltage range including a first predetermined value representing a lean operating condition of the engine, the signaling of the ready condition being inhibited until the sensor input maintains for a predetermined period of time a voltage representing a more lean operating condition than that represented by the first predetermined value.

5. The oxygen sensor analyzer of claim 4, wherein the voltage range is from approximately 0 V representing a most lean operating condition of the engine to approximately 1 V representing a most rich operating condition of the engine, the first predetermined value being approximately 175 mV.

6. The oxygen sensor analyzer of claim 2, wherein the electronic circuit comprises a timer for measuring a passing interval within which the oxygen sensor input changes from a first predetermined value representing a lean operating condition of the engine to a second predetermined value representing a rich operating condition of the engine, the electronic circuit being operative to signal a passing condition only if the oxygen sensor input reaches the second predetermined value within a predetermined period of time.

7. The oxygen sensor analyzer of claim 1, wherein the display comprises a plurality of indicators, each of the indicators being activated by the electronic circuit continuously in response to the oxygen sensor input in accordance with a predetermined range of the oxygen sensor signal.

8. The oxygen sensor analyzer of claim 7, wherein the oxygen sensor input is responsive over a voltage range of approximately 1 volt and at least one of the indicators is activated when the oxygen sensor input is within the voltage range.

9. A portable oxygen sensor analyzer for use in testing the performance of an oxygen sensor comprising a portion of a vehicle emission system having an on-board computer, the oxygen sensor analyzer comprising:
(a) an electronic circuit having an oxygen sensor input for receiving an oxygen sensor signal from the oxygen sensor, with the oxygen sensor disconnected from the on-board computer, over a voltage range of from approximately 0 V representing a most lean operating condition of the engine to approximately 1 V representing a most rich operating condition of the engine, a simulate output for connection to the on-board computer in place of the oxygen sensor, and logic means operative for driving the simulate output in:
  (i) a closed-loop mode wherein the simulate output directly follows the oxygen sensor input;
  (ii) a simulate mode wherein the simulate output, being isolated from the oxygen sensor input, is driven in an arbitrary manner for forcing the engine to run one or both of lean by driving the simulate output to simulate a rich indication from the oxygen sensor, and rich by driving the simulate output to simulate a lean indication from the oxygen sensor;
  (iii) a test mode wherein the simulate output, being isolated from the oxygen sensor input, is driven in a predetermined manner that includes forcing the engine to run lean by driving the simulate output to simulate a rich indication from the oxygen sensor, the logic means being further operative for signaling a ready condition after the engine reaches a stable lean operating condition as signaled by the oxygen sensor input remaining for a predetermined period of time below a first predetermined value representing a lean operating condition of the engine, and subsequently monitoring the oxygen sensor input to measure time-response thereof between conditions of the engine running lean as signaled by the oxygen sensor input passing the first predetermined value and running rich as signaled by the oxygen sensor reaching a second predetermined value being higher than the first predetermined value; and
(b) a display for continuously indicating the oxygen sensor signal.

10. The oxygen sensor analyzer of claim 9, wherein the first predetermined value is approximately 175 mV and the second predetermined value is approximately 800 mV.

* * * * *